United States Patent [19]

Chang et al.

[11] Patent Number: 4,565,641

[45] Date of Patent: Jan. 21, 1986

[54] BLEND OF FLUOROCHEMICAL GUANIDINES AND POLY(OXYALKYLENES)

[75] Inventors: John C. Chang, New Brighton; Kathryn L. Williams, Lakeland, both of Minn.

[73] Assignee: Minnesota Mining and Manufacturing Company, St. Paul, Minn.

[21] Appl. No.: 633,977

[22] Filed: Jul. 24, 1984

Related U.S. Application Data

[63] Continuation-in-part of Ser. No. 440,317, Nov. 9, 1982, abandoned.

[51] Int. Cl.$^4$ .......................................... D06M 13/08
[52] U.S. Cl. .................................... 252/8.75; 252/8.8; 252/8.9
[58] Field of Search .................. 252/8.8, 8.9, 8.75

[56] References Cited

U.S. PATENT DOCUMENTS

| | | | |
|---|---|---|---|
| 2,853,473 | 9/1958 | Campbell et al. | 260/77.5 |
| 2,941,966 | 6/1960 | Campbell | 260/2.5 |
| 3,329,661 | 7/1967 | Smith et al. | 260/79.3 |
| 3,458,571 | 7/1969 | Tokoli | 260/556 |
| 3,574,791 | 4/1971 | Sherman et al. | 260/884 |
| 3,728,151 | 4/1973 | Sherman et al. | 117/138.8 A |
| 3,862,989 | 1/1975 | Hansen | 260/606.5 |
| 3,896,251 | 7/1975 | Landucci | 428/290 |
| 3,916,053 | 10/1975 | Sherman et al. | 428/96 |
| 4,013,627 | 3/1977 | Temple | 526/245 |
| 4,024,178 | 5/1977 | Landucci | 260/472 |
| 4,067,820 | 1/1978 | Wagner et al. | 252/426 |
| 4,144,367 | 3/1979 | Landucci | 428/96 |
| 4,165,338 | 8/1979 | Katsushima et al. | 260/584 |
| 4,174,433 | 11/1979 | Schafer et al. | 528/49 |
| 4,215,205 | 7/1980 | Landucci | 525/331 |
| 4,264,484 | 4/1981 | Patel | 260/29.6 |
| 4,325,857 | 4/1982 | Champaneria et al. | 523/412 |

OTHER PUBLICATIONS

Kirk-Othmer, Encyclopedia of Polymer Science and Technology, 8, 374-404 (1968).
Banks, R. E., Ed. "Organofluorine Chemicals and their Industrial Applications", Ellis Horwood, Ltd., West Sussex, England, 226-230, (1979).
Kurzer et al., Chemical Reviews, 67, 107, (1967).
K. Wagner et al., Angewante Chemie Int. Ed., 20, 819, (1981).

*Primary Examiner*—Prince E. Willis
*Assistant Examiner*—Willie J. Thompson
*Attorney, Agent, or Firm*—Donald M. Sell; James A. Smith; Carole Truesdale

[57] ABSTRACT

Blends of fluoroaliphatic radical-containing, substituted guanidines and fluoroaliphatic radical-containing poly(oxyalkylenes) useful in the form of organic solutions or aqueous dispersions in the treatment of fibrous substrates, such as textile fibers, to impart oil and water repellency.

20 Claims, No Drawings

BLEND OF FLUOROCHEMICAL GUANIDINES AND POLY(OXYALKYLENES)

This application is a continuation in part of copending application Ser. No. 440,317, filed Nov. 9, 1982 now abandoned.

This invention relates to the treatment of fibrous substrates, such as textile fibers, paper, and leather, with fluorochemical compositions to impart oil and water repellency, and to the resulting treated substrates. In another aspect, it relates to the treatment of carpet fiber with a finish comprising a fluoroaliphatic radical-containing composition to impart oil and water repellency and soil resistance to such fiber. In another aspect, it relates to fluoroaliphatic radical-containing compositions, and their preparation, which are useful in such treatment.

In the industrial production of textiles, such as carpet and apparel, and such other fibrous substrates as paper and leather, it is common to treat such substrates with fluorochemicals containing fluoroaliphatic radicals (often designated by the symbol "$R_f$") to impart oil and water repellency to the surface of such substrates. Fluorochemicals of this type and their application to fibrous substrates are described in various prior art publications, e.g., U.S. Pat. Nos. 3,329,661 (Smith et al), 3,458,571 (Tokoli), 3,574,791 (Sherman et al), 3,728,151 (Sherman et al), 3,916,053 (Sherman et al), 4,144,367 (Landucci), 3,896,251 (Landucci), 4,024,178 (Landucci) 4,165,338 (Katsushima et al), 4,215,205 (Landucci), 4,013,627 (Temple), 4,264,484 (Patel), and 4,325,857 (Champaneria et al), and Banks, R. E., Ed. "Organofluorine Chemicals and their Industrial Applications", Ellis Horwood, Ltd., West Sussex, England, 226-230 (1979).

Although some fluorochemicals are useful in many applications and many are commercial products, some are relatively expensive to prepare and apply, others are difficult to apply, and others are not durable or do not impart the required properties to the extent desired.

Conventionally, fluorochemical compositions have been commercially applied as a top coating to the finished fibrous article, such as carpet. Recently, several fluorochemical compositions have been commercially applied to textile fiber or yarn during its manufacture before it is woven or fabricated into the finished article. However, some of these fluorochemical compositions have had limited success for various reasons including incompatibility or reactivity of the fluorochemical with fiber finish components such as lubricants, lack of durability of the fluorochemical on the treated fiber to dyeing or other fiber manufacturing operations, and insufficient water and oil repellency and soil resistance in the finished article.

It is an object of this invention to provide blends of fluoroaliphatic radical-containing, substituted guanidines (hereinafter often called fluorochemical guanidines for brevity) and fluoroalipatic radical-containing poly(oxyalkylenes) (hereinafter often called fluorochemical oxyalkylenes for brevity), said blends being useful for treating textile fibers and other fibrous substrates to impart oil and water repellency thereto.

Another object of this invention is to provide blends of fluorochemical guanidines and fluorochemical oxyalkylenes which can be used to treat textile fibers in combination with or as a component of fiber finishes, e.g. spin-finish lubricants, such blends being compatible with said fiber finishes and not interfering with normal textile fiber processing steps.

A further object of this invention is to provide fluorochemical-treated textile fiber with a high percentage of the fluorochemical retained on the fiber through fiber processing and dyeing steps, and with durable water and oil repellency and soil resistance properties.

It is yet another object of this invention to provide blends of fluorochemical guanidines and fluorochemical oxyalkylenes which can be used in the form of organic solutions or aqueous dispersions to treat fibrous substrates such as textile fibers, filaments, yarns, or finished fibrous articles, e.g. carpets, and other fibrous substrates such as paper and leather, to impart oil and water repellency thereto.

Briefly, this invention provides, in one aspect, compositions comprising blends of: (a) normally solid, water-insoluble, fluorochemical guanidine compositions which are fluoroaliphatic radical-containing, substituted (wholly or partially) guanidine compounds, or compositions comprising or consisting essentially of mixtures of said compounds, which compounds have one or more monovalent fluoroaliphatic radicals ($R_f$) and one or more substituted guanidino moieties, which moieties can be represented in terms of the formula

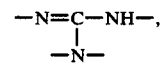

such radicals and moieties bonded together by hetero atom-containing or organic linking groups preferably comprising carbamato (urethane) groups; and (b) normally liquid or low melting solid, water soluble or dispersible, fluoroaliphatic radical-containing poly(oxyalkylene) compounds, or compositions comprising or consisting essentially of mixtures of said oxyalkylene compounds, which compounds have one or more monovalent fluoroaliphatic radical ($R_f$) and one or more poly(oxyalkylene) moieties, such radicals and oxyalkylene moieties bonded together by hetero atom-containing groups or organic linking groups, or combinations of such groups. Said fluorochemical blends are useful in the form of organic solutions or aqueous dispersions in the treatment of fibrous substrates, such as textile fibers (or filaments) during their manufacture, and useful also in the treatment of finished or fabricated fibrous substrates such as carpets, paper, and leather, to impart oil and water repellency to the surface thereof.

A class of such fluorochemical guanidines (component (a) of said blends) can be represented by the general formula

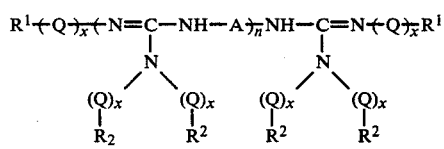

which formula generically encompasses individual compounds or represents a mixture of such compounds as they are obtained from reactions used in their preparation.

Guanidines are conveniently prepared by the reaction of carbodiimides and imino (>NH) compounds, e.g. amines, hydrazines, hydrazides, and amides, using general routes for guanidine synthesis as described, for example, by Kurzer, et al, *Chemical Reviews*, 67, 107, (1967), and in U.S. Pat. No. 4,174,433 (Schafer, et al). In addition, carbodiimides can be prepared from ureas, thioureas, and other compounds as described by K. Wagner et al., *Angewante Chemie Int. Ed.*, 20, 819 (1981). Many fluorochemical guanidines used in this invention can be prepared in an analogous manner from fluorochemical carbodiimides and said imino compounds. Such fluorochemical carbodiimides and their preparation are described in U.S. Pat. No. 4,024,178 (Landucci), which description is incorporated herein by reference thereto.

In formula I, "n" is a number (in the case where the formula is that of a mixture) or an integer (in the case where the formula is that of a compound) of 0 up to 20, preferably 0 to 10 and most preferably 0 to 5, and "x" is 0 or 1. Each Q is the same or different divalent linking group. A is a divalent organic linking group which can contain a fluoroaliphatic radical, $R_f$, each A being the same or different. Each $R^1$ is the same or different and is selected from H, $R_f$, and terminal monovalent organic radicals such as alkyl, cycloalkyl, aryl, and combinations thereof, e.g. aralkyl, which radicals can contain hetero moieties, e.g. —O—, —S—,

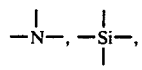

and —CO—, and is preferably free of active (or isocyanate-reactive) hydrogen atoms (i.e., hydrogen atoms of groups, such as mercapto, amino, carboxyl, and aliphatic hydroxyl groups, that can react readily with isocyanate under urethane bond-forming conditions, e.g., 20° to 100° C.). Generally, $R^1$ will have no more than about 18 carbon atoms. Where $R^1$ is said $R_f$, the subscript x of the adjacent Q must be 1 and not 0 because $R_f$ cannot be directly bonded to a N-atom of the guanidino group. Unless otherwise indicated, "R" means either $R^1$ or $R^2$, Each $R^2$ is like $R^1$ but in addition the two $R^2$ groups of a guanidino group can be bonded together to form a cyclic structure with the adjacent N atom of that guanidino group. There is at least one $R_f$ radical present in one or more of the $R^1$, $R^2$, and A groups for a given compound. When only one guanidino moiety is present, and only two organic substituents are in said guanidino moiety, said substituents must be on different N atoms of the moiety.

In the above general formula I, the divalent organic linking group A connects successive guanidino moieties when n is 1 or more. Illustrative linking groups A are alkylene groups, such as ethylene, isobutylene, hexylene, and methylenedicyclohexylene, having 2 to about 20 carbon atoms, aralkylene groups, such as —CH$_2$C$_6$H$_4$CH$_2$— and —C$_6$H$_4$CH$_2$C$_6$H$_4$—, having up to 20 carbon atoms, arylene groups, such as tolylene, —C$_6$H$_3$(CH$_3$)—, poly(oxyalkylene) groups, such as —(C$_2$H$_4$O)$_y$C$_2$H$_4$— where y is 1 to about 5, and various combinations of these groups. Such groups can also include other hetero moieties (besides —O—), including —S— and

However, A is preferably free of groups with said active hydrogen atoms.

The A group can be a residue of an organic diisocyanate (from which the carbodiimido and guanidino moieties can be derived by successive reactions), that is, A can be the divalent radical obtained by removal of the isocyanate groups from an organic diisocyanate. Suitable diisocyanate precursors may be simple, e.g. tolylene-2,4- diisocyanate, methylene bis(4-phenyleneisocyanate), and mixtures thereof, or complex, as formed by the reaction of a simple diisocyanate with an organic diol or polyol in appropriate proportions to yield an isocyanate-terminated polyurethane. Other isocyanates can also be used as starting materials. Some of these are described, for example, in U.S. Pat. No. 4,174,433. Representative A groups include —CH$_2$C$_6$H$_4$CH$_2$C$_6$H$_4$CH$_2$—, —C$_6$H$_3$(CH$_3$)—, —C$_6$H$_{10}$CH$_2$C$_6$H$_{10}$—, —(CH$_2$)$_6$—, —C$_6$H$_4$CH$_2$C$_6$H$_4$—, and C$_8$F$_{17}$SO$_2$N[C$_2$H$_4$OCONHC$_6$H$_3$(CH$_3$)—$_2$. Although the fluorochemical guanidines used in this invention generally and preferably are derived from diisocyanates, the fluorochemical guanidines can be derived from triisocyanates, e.g. OCNC$_6$H$_4$CH$_2$C$_6$H$_3$(-NCO)CH$_2$C$_6$H$_4$NCO. A mixture of di- and tri-isocyanates can be used to provide fluorochemical guanidines which are branched but still retain the desired solubility and dispersibility characteristics of the linear fluorochemical guanidines depicted by formula I.

The R—Q groups are preferably radicals derived from isocyanate compounds and can be aliphatic, e.g. C$_6$H$_{13}$—, aromatic, e.g. C$_6$H$_5$—, aralkyl, e.g. C$_6$H$_5$CH$_2$—, fluoroaliphatic, e.g. C$_6$F$_{13}$CH$_2$—, C$_7$F$_{15}$CH$_2$OCONHC$_6$H$_3$(CH$_3$)—, and C$_8$F$_{17}$SO$_2$N(CH$_3$)C$_2$H$_4$OCONHC$_6$H$_4$CH$_2$C$_6$H$_4$—. The organic R—Q radicals can have a variety of other structures, and can contain hetero atom-containing moieties, e.g. —O—, —S—, and

but, as with the A group, it is preferably free of groups containing said active hydrogen atoms.

The fluoroaliphatic radical, $R_f$, is a fluorinated, stable, inert, non-polar, preferably saturated, monovalent moiety which is both oleophobic and hydrophobic. It can be straight chain, branched chain, and, if sufficiently large, cyclic, or combinations thereof, such as alkylcycloaliphatic radicals. The skeletal chain can include caternary oxygen, hexavalent sulfur, and/or trivalent nitrogen hetero atoms bonded only to carbon atoms, such hetero atoms providing stable linkages between fluorocarbon portions of $R_f$ and not interferring with the inert character of the $R_f$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. The large radicals also are generally less soluble in organic solvents. Generally, $R_f$ will have 3 to 20 carbon atoms, preferably 6 to about 12, and will contain 40 to 78 weight percent, preferably 50 to 78 weight percent, fluorine. The terminal portion of the $R_f$ group has at least three fully fluorinated carbon atoms, e.g. CF$_3$CF$_2$CF$_2$—, and the preferred compounds are those in which the $R_f$ group is fully or substantially completely fluorinated, as in the case where $R_f$ is perfluoroalkyl, $C_nF_{2n+1}$.

Generally, the fluorochemical guanidine will contain about 20 to 70 weight percent, preferably about 25 to 50 weight percent, of carbon-bonded fluorine. If the fluorine content is less than about 20 weight percent, impractically large amounts of the fluorochemical guanidine will generally be required, while fluorine contents greater than about 70 weight percent are unnecessary to achieve the desired surface properties and thus represent an uneconomical use of fluorine and may also present compatibility problems where it is desired to apply the fluorochemical blend as an organic solution.

The function of the linking group Q in formula I is to bond the R groups to the N atoms of the guanidino units. Q can comprise a hetero atom-containing group or an organic group or a combination of such groups, examples of which are polyvalent aliphatic, e.g., —CH$_2$—, —CH$_2$CH$_2$—, and —CH$_2$CH(CH$_2$—)$_2$, polyvalent aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, e.g., —CH$_2$CH$_2$OCONH—, and urea, e.g., —NHCONH—. The linkage Q for a specific fluorochemical guanidine useful in this invention will be dictated by the ease of preparation of such a compound and the availability of necessary precursors thereof. From the above description of Q, it is apparent that this linkage can have a wide variety of structures. However, as with the R and A groups, Q is preferably free of moieties having said active hydrogen atoms. However large Q is, the fluorine content (the locus of which is $R_f$) of the fluorochemical guanidine is in the aforementioned limits.

It should be recognized that, in the above general formula I, isomeric or tautomeric forms may be present. For example, for a given guanidino unit, the following tautomeric forms can exist:

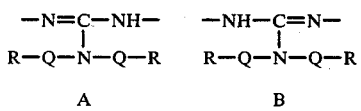

When an R—Q is H, then another isomeric structure can also be present:

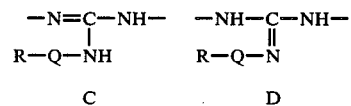

All of the above tautomeric and isomeric forms, as well as mixed $R_f$ groups and other organic moieties, can be present and are included in the fluorochemical guanidines used in this invention.

The fluorochemical guanidines used in this invention are normally solid (i.e., solid at 20° C.) with melting points preferably in the range of 40° to 150° C. They are preferably soluble to the extent of at least 10 weight percent in ethyl acetate at 20° C.

The above-described fluorochemical guanidines can be prepared by successive substitutions on guanidine, or by conversion of precursor carbodiimides to guanidines via reaction with imino compounds (i.e., compounds containing >NH), such as primary or secondary amines. The imino compounds may contain a fluoroaliphatic radical in the instance where the carbodiimide precursor contains a fluoroaliphatic radical, and must contain a fluoroaliphatic radical in the instance where the carbodiimide precursor does not contain a fluoroaliphatic radical.

Fluoroaliphatic radical-containing intermediates ($R_f$ intermediates) generally are commercially made by electrochemical fluorination of organic acids or halides thereof, or by telomerization of tetrafluoroethylene, followed by known reactions to form intermediates that contain a hydroxyl group that is capable of reaction with an isocyanate group to form a urethane linkage (—OCONH—). Such urethane-forming reactions are generally carried out neat or in the presence of non-reactive solvents, such as ethyl acetate or methyl ethyl ketone, at moderate temperatures, such as 20° to 130° C. Catalysts for the urethane formation may be employed, but are unnecessary, and in some cases undesirable when aromatic diisocyanates are employed.

The mixture of urethane group-containing isocyanates and non-urethane-containing isocyanates are then converted to the carbodiimide precursors of the fluorochemical guanidines used in this invention after addition of low levels (e.g., 0.05 to 1.5 weight percent of reactants) of a catalyst. There are many catalysts known to effect carbodiimide formation from isocyanates. Two of the most effective classes are phospholene oxides (described in U.S. Pat. Nos. 2,853,473, 2,941,966, and 4,067,820) and phosphine oxides (described in U.S. Pat. No. 3,862,989). The carbodiimide is then added neat or as an organic solvent solution to the imino compound. This mode of addition as well as moderate temperatures are generally employed to minimize the addition of a guanidino N—H moiety to a carbodiimide which generally leads to reaction mixtures that have considerably lower organic solvent solubility.

Representative reaction schemes for the preparation of fluorochemical guanidines used in this invention are outlined below, where the products designated as I' are species of formula I supra.

Scheme 1

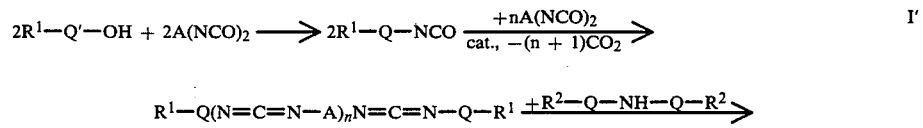

-continued

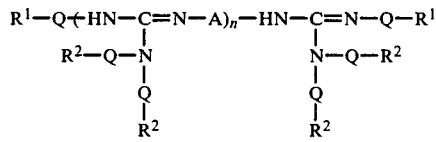

Scheme 2

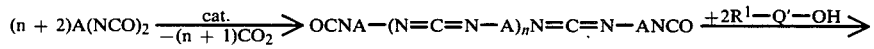

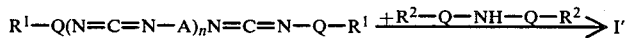

Scheme 3

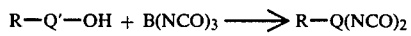

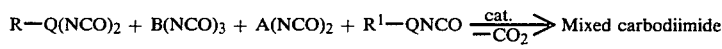

The mixtures of fluorochemical guanidines used in this invention may contain small amounts of fluorochemical diurethane compounds (e.g., R—Q'—OCONH—A—NHCOO—Q'—R, a possible by-product in Scheme 1) free of guanidino groups due to the synthetic procedures generally followed. The amount of this by-product depends on the mode of addition, molar ratio of reactants, and the relative reactivity of isocyanate functional groups. The mixture of fluorochemical guanidines may contain small or minor amounts of compounds that arise from reaction of an initially formed guanidine with a carbodiimide group to give a higher molecular weight fluorochemical guanidine.

Fluorochemical guanidines in which some of the precursor carbodiimide moieties (in cases where n is greater than 1) have not been reacted with an imino compound are also included as fluorochemical guanidines used in this invention.

Representative $R_f$ intermediates for the preparation of fluorochemical guanidines used in this invention include:

$C_8F_{17}SO_2N(C_2H_5)C_2H_4OH$
$C_8F_{17}C_2H_4OH$
$C_7F_{15}CH_2OH$
$C_7F_{15}CON(C_2H_5)C_2H_4OH$
$C_8F_{17}C_2H_4SC_2H_4OH$
$(CF_3)_2CF(CF_2)_8C_2H_4OH$
$(CF_3)_2CFOC_2F_4C_2H_4OH$
$C_8F_{17}C_2H_4SO_2N(CH_3)C_4H_8OH$
$C_8F_{17}SO_2N(CH_3)C_3H_6NH_2$

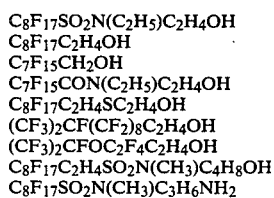

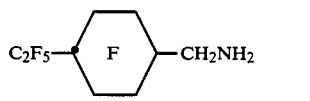

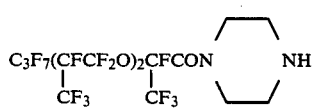

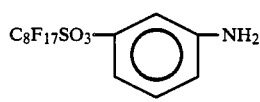

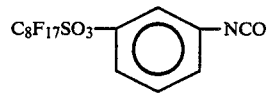

$C_8F_{17}C_6H_4NH_2$
$C_8F_{17}C_6H_4NCO$
$C_7F_{15}CH_2NCO$

Representative organic isocyanates include:
tolylene-2,4-diisocyanate
hexamethylene diisocyanate
methylenebis(4-phenyleneisocyanate)
methylenebis(4-cyclohexyleneisocyanate)
xylylene diisocyanate
1-methoxy-2,4-phenylene diisocyanate
1-chlorophenyl-2,4-diisocyanate,
p-(1-isocyanatoethyl)phenyl isocyanate
phenyl isocyanate
m-tolyl isocyanate
2,5-dichlorophenyl isocyanate
hexyl isocyanate Representative imino compounds include the following: ammonia, methylamine, ethylamine, butylamine, diethylamine, diisopropylamine, dibutylamine, ethyleneimine, morpholine, piperidine, N,N-dimethyl hydrazine, aniline, 3-aminopropyltrimethoxysilane, pyrrolidine, pyrrolidone, imidazole, guanidine, acetamidine, 2-methoxyethylamine, hexamethylenediamine, piperazine, formamide, acetyl hydrazide, sebacoyl dihydrazide.

In cases where certain imino compounds, e.g. ethylene imine, guanidine, N,N'-dialkyl hydrazine, ethylene diamine, and hydrazides, are reacted with fluorochemical carbodiimide precursors (Scheme 1, where the above imino compounds are used), adducts are formed which can rearrange to cyclic guanidino structures. These cyclic forms are also included as fluorochemical guanidine compounds used in this invention.

A class of fluorochemical oxyalkylene, component (b)—the other essential component of the blends of this invention—are fluoroaliphatic oligomers (or polymers, the term oligomer hereinafter including polymer unless otherwise indicated) represented by the general formulas:

$$(R_f)_sZ[(R^3)_yZ'B]_t \qquad \text{II}$$

$$[(R_f)_sZ[(R^3)_yZ'B']_t]_w \qquad \text{III}$$

where $R_f$ is a fluoroaliphatic radical like that described for general formula I, Z is a linkage through which $R_f$ and $(R^3)_y$ moieties are covalently bonded together, $(R^3)_y$ is a poly(oxyalkylene) moiety, $R^3$ being an oxyalkylene group with 2 to 4 carbon atoms and y is an integer (where the above formulas are those of individual compounds) or a number (where the above formulas are those of mixtures) at least 5, generally 10 to 75 and can be as high as 100 or higher, B is a hydrogen atom or a monovalent terminal organic radical, B' is B or a valence bond, with the proviso that at least one B' is a valence bond interconnecting a Z-bonded $R^3$ radical to another Z, Z' is a linkage through which B, or B', and $R^3$ are covalently bonded together, s is an integer or number of at least 1 and can be as high as 25 or higher, t is an integer or number of at least 1, and can be as high as 60 or higher, and w is an integer or number greater than 1, and can be as high as 30 or higher.

In formulas II and III, where there are a plurality of $R_f$ radicals, they are either the same or different. This also applies to a plurality of Z, Z', $R_3$, B, B', and, in formula III, a plurality of s, y and t.

Generally, the oligomers will contain about 5 to 40 weight percent, preferably about 10 to 30 weight percent, of carbon-bonded fluorine. If the fluorine content is less than about 10 weight percent, impractically large amounts of the oligomer will generally be required, while fluorine contents greater than about 35 weight percent result in oligomers which have too low a solubility to be efficient.

In said poly(oxyalkylene) radical, $(R^3)y$, $R^3$ is an oxyalkylene group having 2 to 4 carbon atoms, such as

—OCH$_2$CH$_2$—,

—OCH$_2$CH$_2$CH$_2$—,

—OCH(CH$_3$)CH$_2$—, and —OCH(CH$_3$)CH(CH$_3$)—, the oxyalkylene units in said poly(oxyalkylene) being the same, as in poly(oxypropylene), or present as a mixture, as in a heteric straight or branched chain or randomly distributed oxyethylene and oxypropylene units or as in a straight or branched chain of blocks of oxyethylene units and blocks of oxypropylene units. The poly(oxyalkylene) chain can be interrupted by or include one or more catenary linkages. Where said catenary linkages have three or more valences, they provide a means for obtaining a branched chain or oxyalkylene units. The poly(oxyalkylene) radicals in the oligomers can be the same or different, and they can be pendent. The molecular weight of the poly(oxyalkylene) radical can be about 500 to 2500 and higher, e.g. 100,000 to 200,000 or higher.

The function of the linkages Z and Z' is to covalently bond the fluoroaliphatic radicals, $R_f$; the poly(oxyalkylene) moieties, $(R^3)y$ and radicals B and B' together in the oligomer. Z and Z' can be a valence bond, for example, where a carbon atom of a fluoroaliphatic radical is bonded or linked directly to a carbon atom of the poly(oxyalkylene) moiety. Z and Z' each can also comprise one or more linking groups such as polyvalent aliphatic and polyvalent aromatic, oxy, thio, carbonyl, sulfone, sulfoxy, phosphoxy, amine, and combinations thereof, such as oxyalkylene, iminoalkylene, iminoarylene, sulfoamido, carbonamido, sulfonamidoalkylene, carbonamidoalkylene, urethane, urea, and ester. The linkages Z and Z' for a specific oligomer will be dictated by the ease of preparation of such an oligomer and the availability of necessary precursors thereof.

From the above description of Z and Z' it is apparent that these linkages can have a wide variety of structures, and in fact where either is a valence bond, it doesn't even exist as a structure. However large Z or Z' is, the fluorine content (the locus of which is $R_f$) is in the aforementioned limits set forth in the above description, and in general the total Z and Z' content of the oligomer is preferably less than 10 weight percent of the oligomer.

The monovalent terminal organic radical, B, is one which is covalently bonded through Z', to the poly(oxyalkylene) radical.

Though the nature of B can vary, it preferably is such that it compliments the poly(oxyalkylene) moiety in maintaining or establishing the desired solubility of the oxyalkylene. The radical B can be a hydrogen atom, acyl, such as $C_6H_5C(O)$—, alkyl, preferably lower alkyl, such as methyl, hydroxyethyl, hydroxypropyl, mercaptoethyl and aminoethyl, or aryl, such as phenyl, chlorophenyl, methoxyphenyl, nonylphenyl, hydroxyphenyl, and aminophenyl. Generally, Z'B will be less than 50 weight percent of the $(R^3)_yZ'B$ moiety.

The fluoroaliphatic radical-containing oxyalkylene used in this invention can be prepared by a variety of known methods, such as by condensation, free radical, or ionic homopolymerization or copolymerization using solution, suspension, or bulk polymerization techniques e.g., see "Preparative Methods of Polymer Chemistry", Sorenson and Campbell, 2nd ed., Interscience Publishers, (1968). Classes of representative oxyalkylene useful in this invention include polyesters, polyurethanes, polyepoxides, polyamides and vinyl polymers such as polyacrylates and substitute polystyrenes.

The polyacrylates are a particularly useful class of oxyalkylenes and they can be prepared, for example, by free radical initiated copolymerization of a fluoroaliphatic radical-containing acrylate with a poly(oxyalkylene) acrylate, e.g. monoacrylate or diacrylate or mixtures thereof. As an example, a fluoroaliphatic acrylate, $R_f$—R"—O$_2$C—CH=CH$_2$ (where R" is, for example, sulfonamidoalkylene, carbonamidoalkylene, or alkylene), e.g., $C_8F_{17}SO_2N(C_4H_9)CH_2CH_2O_2CCH=CH_2$, can be copolymerized with a poly(oxyalkylene) monoacrylate, $CH_2=CHC(O)(R^3)_xOCH_3$, to produce a polyacrylate oxyalkylenes.

Further description of fluorochemical oxyalkylenes useful in this invention will be omitted in the interest of brevity since such compounds and their preparation are known, said U.S. Pat. No. 3,787,351 and U.S. Pat. No. 4,289,892, both of which are incorporated herein for that purpose.

The amount of each component (a) and (b) can vary over a broad range, and will be selected to provide the desired balance of properties on the treated fiber of finished article. Generally, component (a) will be the major amount of the blend and component (b) will be the minor amount. The particular amount depends on the particular commposition of the textile fiber or article to be treated and the particular chemical composition of (a) and (b), as well as the application procedures used. Laboratory evaluation will often be a good indicator of appropriate relative amounts of components (a) and (b) to be used for obtaining the desired performance in commercial application.

Generally, the relative amounts of components (a) and (b) fall within the following ranges:

| Component | Weight percent of fluorochemical solids in blend | |
|---|---|---|
| | Broad Range | Preferred Range |
| (a) | 60–99 | 70–95 |
| (b) | 1–40 | 5–30 |

The blends of this invention can be obtained by mixing (1) an organic solvent solution or aqueous dispersion of the fluorochemial guanidine with (2) the fluorochemical poly(oxyalkylene) which may be utilized in neat form or as an organic solvent solution or as an aqueous dispersion. If an aqueous emulsion is the desired form of the blend, the emulsification may be performed on the above organic solvent-containing blends, or individually emulsified components may be blended (by simple mixing techniques) as either solvent-containing or solvent-free emulsions. In the preparation of said emulsions it is generally beneficial to employ cationic fluorochemical surfactants (i.e., $C_8F_{17}SO_2N(H)C_3H_6N(CH)_3Cl$) along with hydrocarbon non-ionic surfactants (i.e., "Tween 80" polyoxyethylene sorbitan monooleate). Since the fluorochemical poly(oxyalkylenes) and mixtures thereof are themselves non-ionic surfactants, the hydrocarbon non-ionic co-surfactants may be totally or partially eliminated by the incorporation of the fluorochemical poly(oxyalkylene) into the solvent-containing blend prior to emulsification.

Substrates which can be treated in accordance with this invention are textile fibers (or filaments), and finished or fabricated fibrous articles such as textiles, e.g. carpet, paper, paperboard, leather, and the like. The textiles include those made from natural fibers, such as cotton and wool, and those made from synthetic organic fibers, such as nylon, polyolefin, acetate, rayon, acrylic, and polyester fibers. Especially good results are obtained on nylon and polyester fibers. The fibers or filaments as such or in an aggregated form, e.g. yarn, tow, web, or roving, or the fabricated textile, e.g., articles such as carpet and woven fabrics, can be treated with the fluorochemical blends. The treatment can be carried out by applying the fluorochemical blends as organic solutions or aqueous or organic dispersions by known techniques customarily used in applying fluorochemicals, e.g. fluorochemical acrylate copolymers, to fibers and fibrous substrates. (If desired, such known fluorochemicals can be used in conjunction with the fluorochemical blends, as will be shown below). For example, the fluorochemical treatment can be by immersing the fibrous substrates in a bath containing the fluorochemical blend, padding the substrate or spraying the same with the fluorochemical blend, or by foam, kiss-roll, or metering applications, e.g. spin finishing, and then drying the treated substrates if solvent is present. If desired, the fluorochemical blend can be co-applied with conventional fiber treating agents (or adjuvants), e.g. antistatic agents or neat oils (non-aqueous fiber lubricants).

In the manufacture of synthetic organic fibers (see, for example, the review article in Kirk-Othmer, *Encyclopedia of Polymer Science and Technology*, 8, 374–404, 1968), the first step that normally takes place in the process, following initial formation of the filaments (e.g. by melt spinning or solvent spinning), is coating the fiber surface with a small amount (generally less than 2% active solids on fiber) of fiber finish comprising lubricating and antistatic agents. It is particularly advantageous to treat such textile fibers, e.g. nylon 6, with the fluorochemical blend of this invention in conjunction with the spin finish being applied to such textile fibers.

Fiber finishes are generally produced in the form of dilute aqueous emulsions or as an oil ("neat oil") which principally contains said lubricant and antistatic agent as well as emulsifier (surfactant) and may also contain materials such as bacteriocides and antioxidants.

Representative lubricants include mineral oils, waxes, vegetable oils (triglycerides) such as coconut oil, peanut oil, and castor oil, synthetic oils, such as esters, polyoxyethylene derivatives of alcohols and acids, and silicone oils.

The antistatic agents, emulsifiers, and surfactants incorporated into the fiber finish are selected from similar chemical classes, which include:

(a) anionics, such as fatty acid soaps, sulfated vegetable oils, salts of alkyl and ethoxylated alkyl phosphates;

(b) cationics, such as fatty amines, quaternary ammonium compounds, and quaternary phosphonium compounds;

(c) nonionics, such as glyceryl monooleate, ethoxylated alcohols, ethoxylated fatty acids, and ethoxylated fatty amides; and (d) amphoterics, such as betaines, amino acids and their salts.

The preferred mode of applying the fluorochemical blend of this invention to synthetic organic fibers is to incorporate the blend into the above-described fiber finishes in an amount sufficient to achieve the desired properties, oil and water repellency and soil resistance. Generally, the amount of fluorochemical blend to be used will be that sufficient to retain on the fiber of the finished article, e.g., carpet, about 200 to 1600 ppm fluorine based on the weight of the fiber. Such additions to the conventional fiber finish can be carried out without sacrificing or adversely affecting typical requirements that conventional fiber finishes must meet, namely lubrication, thermal stability, low fuming at elevated temperature, and wetting for fiber dyeability (color addition). The conventional finish components of the fiber finishes containing the fluorochemical blends of this invention can be removed in a conventional manner after the fiber is manufactured in fabric form, e.g., carpets and upholstery fabrics. The fluorochemical blends withstand the typical conditions encountered during fiber and yarn processing and also survive the more severe processing conditions which the greige goods encounter such as scouring and dyeing, and the finished goods encounter, such as washing, steam cleaning, and dry cleaning. The fluorochemical blends do not interfere with, and are durable through, the normal fiber processing steps, e.g., drawing, texturizing, and heat setting, and provide oil and water repellency and anti-soiling properties to the finished article, e.g., carpet made from the treated fibers.

The conventional application methods used to apply finishes to fibers (or filaments) can be used with the fluorochemical blend finishes of this invention. Such methods include the use of either (a) a revolving ceramic cylinder, i.e., kiss-roll, which is partially immersed in a pan containing the finish, over which the moving filaments pass and pick up a thin film of finish, (b) a metering pump supplying finish through a slot or hole in a fiber guide over which the moving filaments pass, (c) an immersion finish bath, or (d) spraying devices.

The fluorochemical blends of this invention are generally compatible with (i.e., dispersible or sufficiently soluble in) commercial neat oil fiber finishes, yielding stable dispersions or solutions thereof, and thus the blends may be mixed with such finishes and coapplied (or applied before or after them). Solubilizing aids, such as "Carbitol" or "Cellosolve" solvents, can be added to the finish to enhance solubility of the fluorochemical blends in the neat oil finish.

Representative fluorochemical guanidines of this invention having the general formula IV are shown in Table 1.

$$R-Q-A(NH-\underset{\underset{R^2-N-R^2}{|}}{C}=N-A)_n-Q-R \quad \text{IV}$$

which comprise mixtures thereof, the lengths of the fluoroaliphatic radical, and the poly(oxyalkylene) moiety varying and the subscripts denoting the number of carbon atoms of the former and denoting the number of oxalkylene units in a poly(oxyalkylene) segment being in both cases average numbers, and in this specification, e.g. Table 2, those subscripts should be understood as having such average values, unless otherwise indicated.

TABLE 2

| | |
|---|---|
| 1. | $C_8F_{17}SO_2N(C_2H_5)CH_2CO_2(C_2H_4O)_{15}H$ |
| 2. | $C_8F_{17}SO_2N(C_2H_5)C_2H_4O(C_2H_4O)_{14}H$ |
| 3. | $C_8F_{17}C_2H_4O(C_2H_4O)_{15}H$ |
| 4. | $C_8F_{17}SO_2N\begin{matrix}(C_2H_4O)_mH\\(C_2H_4O)_nH\end{matrix}$ (m + n = 25) |
| 5. | $C_8F_{17}SO_2N(C_2H_5)C_2H_4O(C_3H_6O)_8H$ |
| 6. | $C_8F_{17}C_2H_4SCHCO_2(C_3H_6O)_mH$<br>$\quad\quad\quad\quad\; \mid$<br>$\quad\quad\quad\quad CH_2CO_2(C_3H_6O)_nH$ (m + n = 20) |

Representative fluorochemical oxyalkylene polyacrylates useful as component (b) in this invention are those made by copolymerizing any of the fluorochemical acrylates of Table 3 with any of the fluorine-free poly(oxyalkylene) monomers of Table 4

TABLE 3

TABLE 1

| Compound No.* | R—Q | A | NR²R² |
|---|---|---|---|
| 1 | $C_8F_{17}$—$SO_2N(C_2H_5)C_2H_4OCONH$ | $C_6H_4CH_2C_6H_4$ | $N(C_4H_9)_2$ |
| 2 | $C_8F_{17}$—$SO_2N(C_2H_5)C_2H_4OCONH$ | $C_6H_4CH_2C_6H_4$ | $N(iC_3H_6)_2$ |
| 3 | $C_8F_{17}$—$SO_2N(C_2H_5)C_2H_4OCONH$ | $C_6H_4CH_2C_6H_4$ | $N(C_2H_5)_2$ |
| 4 | $C_8F_{17}$—$SO_2N(C_2H_5)C_2H_4OCONH$ | $C_6H_3(CH_3)$ | $NHCH(CH_3)_2$ |
| 5 | $C_8F_{17}$—$SO_2N(C_2H_5)C_2H_4OCONH$ | $C_6H_3(CH_3)$ | $NHC_{12}H_{25}$ |
| 6 | $C_8F_{17}$—$SO_2N(C_2H_5)C_2H_4OCONH$ | $C_6H_4CH_2C_6H_4$ | 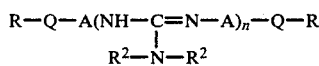 |
| 7 | $C_8F_{17}$—$SO_2N(C_2H_5)C_2H_4OCONH$ | $C_6H_4CH_2C_6H_4$ | $NHN(CH_3)_2$ |
| 8 | $C_8F_{17}$—$SO_2N(C_2H_5)C_2H_4OCONH$ | $C_6H_3(CH_3)$ | $NHC_3H_6Si(OMe)_3$ |
| 9 | $C_8F_{17}$—$SO_2N(C_2H_5)C_2H_4OCONH$ | $C_6H_4CH_2C_6H_4$ | N⟨ ⟩NSO₂C₈F₁₇ |
| 10 | $(CH_3)_2CHCH_2$—$OCONH$ | $C_6H_4CH_2C_6H_4$ | N⟨ ⟩NSO₂C₈F₁₇ |
| 11 | $C_8F_{17}$—$SO_2N(C_2H_5)C_2H_4OCONH$ | $C_6H_4CH_2C_6H_4$ | $\underset{H}{N}$—⟨⟩—$O_3SC_8F_{17}$ |
| 12 | $C_8F_{17}$—$SO_2N(C_4H_9)C_2H_4OCONH$ | $C_6H_4CH_2C_6H_4$ | $N(C_4H_9)_2$ |
| 13 | $C_8F_{17}$—$C_2H_4OCONH$ | $C_6H_4CH_2C_6H_4$ | $N(C_4H_9)_2$ |
| 14 | $C_8F_{17}$—$C_2H_4OCONH$ | $C_6H_3(CH_3)$ | $N(C_4H_9)_2$ |

*For all compounds listed, n has an average value of 2, except for compound no. 4, where n has a value of about 1.8.

Representative fluorochemical oxyalkylenes useful as component (b) in the fluorochemical blends of this invention are shown in Table 2. Generally the preparation of the fluorochemical oxyalkylenes results in products 1. $C_8F_{17}SO_2N(CH_3)CH_2CH_2OOCCH=CH_2$,
2. $C_6F_{13}C_2H_4OOCC(CH_3)=CH_2$, TABLE 3-continued 3. $C_6F_{13}C_2H_4SC_2H_4OOCCH=CH_2$,
4. $C_8F_{17}C_2H_4OOCC(CH_3)=CH_2$
5. $C_8F_{17}C_2H_4N(CH_3)C_2H_4OOCC(CH_3)=CH_2$,
6. $C_2F_5C_6F_{10}CH_2OOCCH=CH_2$,
7. $C_7F_{15}CH_2OOCCH=CH_2$
8. $C_7F_{15}CON(CH_3)C_2H_4OOCCH=CH_2$,
9. $(CF_3)_2CF(CF_2)_6CH_2CH(OH)CH_2OOCCH=CH_2=CH_2$,
10. $(CF_3)_2CFOC_2F_4C_2H_4OOCCH=CH_2$,
11. $C_8F_{17}C_2H_4SO_2N(C_3H_7)C_2H_4OOCCH=CH_2$,
12. $C_7F_{15}C_2H_4CONHC_4H_8OOCCH=CH_2$, 13. $C_3F_7(CFCF_2O)_2CFCH_2OOCCH=CH_2$,
       |         |
       $CF_3$    $CF_3$ 14. $C_7F_{15}COOCH_2C(CH_3)_2CH_2OOCC(CH_3)=CH_2$,
15. $C_8F_{17}SO_2N(C_2H_5)C_4H_8OOCCH=CH_2$,
16. $(C_3F_7)_2C_6H_3SO_2N(CH_3)C_2H_4OOCCH=CH_2$, 17.     $CF_2CF_2$
       /        \
  $C_2F_5CF$      $NC_2F_4CON(CH_3)C_2H_4OOCCH=CH_2$,
       \        /
        $CF_2CF_2$ 18. $C_6F_{17}CF=CHCH_2N(CH_3)C_2H_4OOCCH=CH_2$,
19. $C_8F_{17}SO_2N(C_4H_9)C_2H_4OCOCH=CH_2$
20. $C_8F_{17}SO_2N(C_2H_5)C_2H_4OCOCH(CH_3)=CH_2$

TABLE 4

1. $CH_2=CHCO_2(C_2H_4O)_{10}(C_3H_6O)_{22}(C_2H_4O)_9C_2H_4O_2CCH=CH_2$
2. $CH_2=CHCO_2(C_2H_4O)_{17}H$
3. $CH_2=C(CH_3)CONH(C_3H_6)_{44}H$
4. $CH_2=C(CH_3)CO_2(C_2H_4O)_{90}COC(CH_3)=CH_2$
5. $HS(C_2H_4O)_{23}(C_3H_6O)_{35}(C_2H_4O)_{22}C_2H_4SH$

Other compatible optional comonomers, e.g. butyl acrylate, acrylonitrile, etc. which need not contain fluoroaliphatic radicals, can be copolymerized with the fluorochemical acrylate and oxyalkylene comonomers in amounts up to above 25 weight percent.

Weight ratios of fluorochemical acrylate monomers (Table 3) and fluorochemical poly(oxyalkylene) monomers (Table 4) can vary but should be chosen along with said optional comonomers so that the carbon-bonded fluorine content of the resulting copolymer is in the desired range of 5 to 40 weight prcent.

Objects and advantages of this invention are illustrated in the following examples.

EXAMPLE 1

In a 2-liter, 3-neck flask, fitted with a mechanical stirrer, condenser, thermometer, addition funnel and electric heating mantle, was placed 375 g (1.5 moles) methylenebis(4-phenyleneisocyanate) and 481 g methyl ethyl ketone (MEK). To this stirred heated solution (80°-83° C.) was added 554 g (1.0 mole) N-ethyl(perfluorooctane)sulfonamidoethyl alcohol over a 3 hour period and stirring and heating continued for an additional 3 hours.

To this stirred solution, containing fluorochemical urethane isocyanate and unreacted diisocyanate, was added 7.4 g camphene phenyl phosphine oxide, $C_{10}H_{16}POC_6H_5$, a carbondiimide-forming catalyst, and the reaction mixture was stirred and heated at about 80° C. for about 8 hours, at which time essentially all of the isocyanate groups had been converted to carbodiimide groups as indicated by IR absorption analysis.

The resulting solution of fluorochemical carbodiimide was then allowed to cool to room temperature and added over a one hour period to a stirred solution of 129 g (1.0 mole) dibutylamine in 129 g MEK maintained at 30° C. The resulting reaction mixture was heated for one hour at 50° C. to complete the conversion of essentially all carbodiimide groups to quanidine groups as indicated by IR analysis. The solid fluorochemical guanidine product (represented by structure 1 in Table 1), isolated in quantitative yield by evaporation of the MEK solvent under reduced pressure, was found to have a melting range of 75°-83° C.

EXAMPLES 2-14

Following the general procedure of Example 1, except employing the reagents in Table 5 and molar concentrations indicated in Table 6, the other fluorochemical guanidines of Table 1 were prepared. The reagents in Table 5 are identified by symbols, e.g. A-1, etc., for later reference.

TABLE 5

Alcohol Reagents

A-1 $C_8F_{17}SO_2N(C_2H_5)C_2H_4OH$
A-2 $C_8F_{17}SO_2N(C_4H_9)C_2H_4OH$
A-3 $C_8F_{17}C_2H_4OH$
A-4 $(CH_3)_2CHCH_2OH$

Isocyanates

MDI 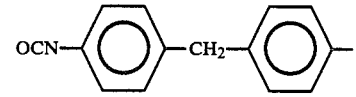

$OCN-\bigcirc-CH_2-\bigcirc-NCO$

TDI 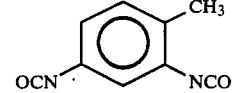

$OCN-\bigcirc(CH_3)-NCO$

Imino Reagents

I-1 $(C_4H_9)_2NH$
I-2 $(iso-C_3H_7)_2NH$
I-3 $(C_2H_5)_2NH$
I-4 $(CH_3)_2CHNH_2$
I-5 $C_{12}H_{25}NH_2$ I-6 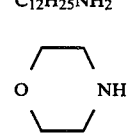

O⟨  ⟩NH

I-7 $(CH_3)_2NNH_2$
I-8 $(CH_3O)_3SiC_3H_6NH_2$

I-9 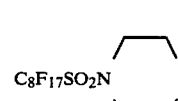

$C_8F_{17}SO_2N$⟨  ⟩NH

I-10 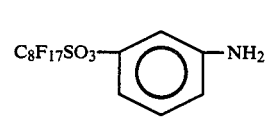

$C_8F_{17}SO_3-\bigcirc-NH_2$

TABLE 6

| Ex. No | Compound used* | Reactants (moles)** | | |
|---|---|---|---|---|
| | | Alcohol Reagent | Isocycanate | Imino Reagent |
| 2 | 2 | A-1 | MDI | I-2 |
| 3 | 3 | A-1 | MDI | I-3 |
| 4 | 4 | A-1 (2) | TDI (2.8) | I-4 (1.8) |
| 5 | 5 | A-1 | TDI | I-5 |
| 6 | 6 | A-1 | MDI | I-6 |
| 7 | 7 | A-1 | MDI | I-7 |
| 8 | 8 | A-1 | TDI | I-8 |

TABLE 6-continued

| Ex. No | Compound used* | Reactants (moles)** | | |
|---|---|---|---|---|
| | | Alcohol Reagent | Isocycanate | Imino Reagent |
| 9 | 9 | A-1 | MDI | I-9 |
| 10 | 10 | A-4 | MDI | I-9 |
| 11 | 11 | A-1 | MDI | I-10 |
| 12 | 12 | A-2 | MDI | I-1 |
| 13 | 13 | A-3 | MDI | I-1 |
| 14 | 14 | A-3 | TDI | I-1 |

*The numbers correspond to the formula numbers of Table 1.
**All alcohol/isocaynate/imino reagent molar ratios were 2/3/2, except as indicated for Example 4.

EXAMPLE 15

This example describes the treatment of a nylon 6 carpet fiber with a blend of fluorochemical guanidine and fluorochemical oxyalkylene of this invention dissolved in a spin finish lubricant and the testing of the dried carpet prepared from the treated fibers.

The oil repellency (OR), water repellency (WR) and walk-on soil resistance (WOS) were determined on the treated samples.

The water repellency test is one which is often used for this purpose. The aqueous stain or water repellency of treated samples is measured using a water/isopropyl alcohol test, and is expressed in terms of a water repellency rating of the treated carpet or fabric. Treated carpets which are penetrated by or resistant only to a 100 percent water/0 percent isopropyl alcohol mixture (the least penetrating of the test mixtures) are given a rating of 100/0, whereas treated fabrics resistant to a 0 percent water/100 percent isopropyl alcohol mixture (the most penetrating of the test mixtures) are given a rating of 0/100. Other intermediate values are determined by use of other water/isopropyl alcohol mixtures, in which the percentage amounts of water and isopropyl alcohol are each multiples of 10. The water repellency rating corresponds to the most penetrating mixture which does not penetrate or wet the fabric after 10 seconds contact. In general a water repellency rating of 90/10 or better, e.g, 80/20, is desirable.

The oil repellency test is also one which is often used for this purpose. The oil repellency of treated carpet and textile samples is measured by AATCC Standard Test 118-1978, which test is based on the resistance of treated fabric to penetration by oils of varying surface tensions. Treated fabrics resistant only to "Nujol", a brand of mineral oil and the least penetrating of the test oils, are given a rating of 1, whereas treated fabrics resistant to heptane (the most penetrating of the test oils) are given a value of 8. Other intermediate values are determined by use of other pure oils or mixtures of oils. The rated oil repellency corresponds to the most penetrating oil (or mixture of oils) which does not penetrate or wet the fabric after 10 seconds contact rather than the 30 seconds contact of the Standard Test. Higher numbers indicate better oil repellency. In general, an oil repellancy of 2 or greater is desirable.

The soil resistance of treated and untreated (control) carpet was determined by exposure to pedestrian traffic according to AATCC Test Method 122-1979, the exposure site being a heavily travelled industrial area for an exposure of about 15,000 "traffics". The samples are repositioned periodically to insure uniform exposure and are vacuumed every 24 hours during the test and before visual evaluation. The evaluation employed the following "Walk-On-Soiling" (WOS) rating system:

| WOS Rating | Description |
|---|---|
| 0 | equal to control |
| ±½ | slightly better (+) or worse (−) than control |
| ±1 | impressive difference compared to control |
| ±1½ | very impressive difference compared to control |
| ±2 | extremely impressive difference compared to control |

A neat oil spin finish consisting of 13.1% fluorochemical guanidine of formula 1 of Table 1, 5.0% fluorochemical poly(oxyalkylene)/acrylate copolymer, viz, a 30/40/30 copolymer of $C_8F_{17}SO_2N(C_4H_9)C_2H_4OCOCH=CH_2$, $CH=CHCO_2(C_2H_4O)_{10}(C_3H_6O)_{22}(C_2H_4OH)$, and $CH=CHCO_2(C_2H_4O)_{10}(C_3H_6O)_{22}(C_2H_4O)_9C_2H_4O_2CCH=CH_2$, 46.2% of a coconut oil-based fiber lubricant, and 35.7% butoxyethoxyethanol was applied by a metered slot applicator to freshly melt-extruded, undrawn yarn of nylon 6 carpet denier fibers. The thus treated yarn was continuously drawn and texturized, plied to form a two-ply yarn, heat set at 190° C. for one minute, and then made into cut pile carpet. The carpet was acid dyed by three different processes, dried, and then evaluated for oil and water repellency, walk-on-soil resistance, and retention of fluorochemical treatment (as measured by fluorine analysis) through the dyeing process. The runs are summarized and the testing results are in Table 7, Runs 1-3. Comparative Runs, C1-C3, utilized a spin finish of the same composition except that the fluorochemical poly(oxyalkylene) component was omitted and 5.0% additional butoxyethoxyethanol was added instead.

| Run | Amount Fluorine on Carpet | | | OR | WR | WOS |
|---|---|---|---|---|---|---|
| | Before Dyeing, ppm | After Dyeing, ppm | Retention of Fluorine, % | | | |
| 1 | 425 | 345[a] | 81 | 3.5 | 50/50 | +1½ |
| 2 | 425 | 335[b] | 79 | 3 | 50/50 | +1 |
| 3 | 425 | 325[c] | 77 | 4 | 50/50 | +1½ |
| C-1 | 430 | 420[a] | 98 | 2 | 73/30 | 0 |
| C-2 | 430 | 400[b] | 93 | 2.5 | 40/60 | +1 |
| C-3 | 430 | 350[c] | 81 | 2.5 | 40/60 | 0 |

[a]Continuous dye process was used for dyeing.
[b]Beck dye (batch) process was used for dyeing.
[c]Continuous pad dye process was used for dyeing.

The test results show that the fluorochemical blend of this invention, Runs 1-3, imparted desirable oil and water repellency and soil resistance to the nylon fiber and the fluorochemical was retained at high levels through dyeing. The results also show significantly better OR and WOS values for Runs 1-3 compared to Runs C-1, C-2, C-3 (even at the lower fluorochemical retention level on fiber), demonstrating the value of the fluorochemical poly(oxyalkylene) component in the finish of this invention.

EXAMPLE 16

In this example, two different rainwear fabrics were treated by a padding operation in Runs 1, 2 with an aqueous dispersion of a blend of 20 parts of the fluorochemical guanidine of formula 6 of Table 1 and 1 part of the fluorochemical poly(oxyalkylene)/acrylate copolymer of Example 15. An aqueous dispersion of said fluorochemical guanidine was used in comparative Runs C-1 and C-2. The treated fabrics were dried at 150° C. for 10 minutes. The treated rainwear fabrics were evaluated again after 5 launderings (5L) and dry cleaning (DC). The OR test used was the above-described AATCC Standard Test 118-1978, the contact time before observation being the specified 30 sec., an OR value of 3 greater being particularly desirable.

The water spray rating (SR) is measured by AATCC Test Method 22-1979. The spray rating is measured using a 0 to 100 scale where 100 is the highest possible rating. In general, a spray rating of 70 or greater is desirable, particularly for outerwear fabrics.

The treated fabrics were laundered using a mechanically agitated automatic washing machine capable of containing a 4 Kg. load, using water at 50° C. and a commercial detergent, and then the washed fabrics were tumble-dried in an automatic dryer for 40 minutes at 70° C. and pressed in a flat-bed press (at 154° C.) before testing.

The treated fabrics were dry cleaned using perchloroethylene containing 1% of a dry cleaning detergent and tumbling in a motor driven tumble jar (AATCC Test Method 70-1975) for 20 minutes at 25° C. After removing excess solvent in a wringer, samples were dried at 70° C. for 10 minutes, then pressed on each side for 15 seconds on a flat-bed press maintained at 154° C.

The runs are summarized and the test results are given in Table 8.

TABLE 8

| Run | Fluorochemical Used | Fabric[a] | % SIB[c] | % SOF[b] | Initial OR | Initial SR | 5L OR | 5L SR | DC OR | DC SR |
|---|---|---|---|---|---|---|---|---|---|---|
| 1 | Blend | A | 1.01 | 0.21 | 6 | 60 | 4 | 60 | 2 | 50 |
| 2 | Blend | B | 0.23 | 0.21 | 5 | 70 | 4 | 70 | 2 | 70 |
| C-1 | FC-G 6* | A | 0.96 | 0.20 | 4.5 | 60 | 3.5 | 70 | 1.5 | 50 |
| C-2 | FC-G 6* | B | 0.22 | 0.20 | 5 | 75 | 3 | 70 | 1.5 | 70 |
| C-3 | None | A | 0 | 0 | 0 | 0 | 0 | 0 | 0 | 0 |
| C-4 | None | B | 0 | 0 | 0 | 0 | 0 | 0 | 0 | 0 |

*FC-G 6 is the fluorochemical guanidine having formula 6 of Table 1.
[a]Fabric A was 100% nylon taffeta.
Fabric B was 100% woven polyester.
[b]% SOF means % fluorochemical solids on fabric.
[c]% SIB means % fluorochemical solids in bath.

The data of Table 8 show useful oil and water repellency was obtained for the rainwear, though laundering and dry cleaning decreased the oil repellency. Furthermore, the oil and water repellancy after laundering or dry cleaning of the fabrics treated with the blend (Runs 1, 2) is better than that of fabric treated with just the fluorochemical guanidine (Runs C-1, C-2).

Various modifications and alterations of this invention will become apparent to those skilled in the art without departing from the scope of this invention.

What is claimed is:

1. A composition comprising a blend of: (a) a normally solid, water-insoluble, fluorochemical guanidine composition which is a fluoroaliphatic radical-containing, substituted guanidine compound, or composition comprising a mixture of such compounds, said compound having one or more monovalent fluoroaliphatic radicals, having at least three fully fluorinated carbon atoms, and one or more substituted guanidino moieties, which moieties can be represented in terms of the formula

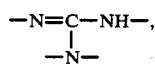

said radicals and moieties being bonded together by linking groups selected from aliphatic, aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, and urea groups, and combinations thereof, with the proviso that when only one guanidino moiety is present, and only two organic substituents are in said guanidino moiety, said substituents must be on different nitrogen atoms of the moiety, and when more than one guanidino moiety is present, said moieties are bonded together by divalent linking groups selected from the group consisting of alkylene, aralkylene, arylene, polyoxyalkylene, and combinations thereof and can contain said fluoroaliphatic radical; and (b) a normally liquid or low melting solid, water soluble or dispersible, fluoroaliphatic radical-containing poly(oxyalkylene), or composition comprising a mixture of such poly(oxyalkylenes), said poly(oxyalkylene) having one or more of said fluoroaliphatic radicals and one or more poly(oxyalkylene) moieties, said radicals and poly(oxyalkylene) moieties bonded together by linking groups selected from aliphatic, aromatic, oxy, thio, carbonyl, sulfone, sulfoxy, phosphoxy, and amine groups and combinations thereof.

2. A composition according to claim 1 wherein said fluorochemical guanidine compounds are represented by the general formula

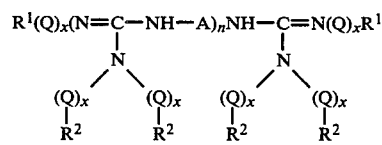

where n is 0 to 20, x is 0 or 1, A is a divalent organic linking group selected from alkylene, aralkylene, arylene, and polyoxyalkylene groups and combinations thereof, which can contain hetero moieties and said fluoroaliphatic group, R$_f$, R$^1$ and R$^2$ are hydrogen atoms, said R$_f$, or an organic radical selected from alkyl, cycloalkyl, and aryl groups and combinations thereof which can contain hetero moieties, the two R$^2$ groups of a guanidino moiety can be bonded together to form a cyclic structure with the adjacent N-atom of said guanidine moiety, Q is a linking group selected from aliphatic, aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, and urea groups, and thereof.

3. A composition according to claim 2 wherein said fluorochemical guanidine is represented by the formula

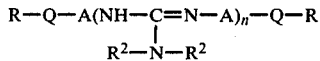

where R—Q is $C_8F_{17}SO_2N(C_2H_5)C_2H_4OCONH—$, A is $—C_6H_4CH_2C_6H_4—$,

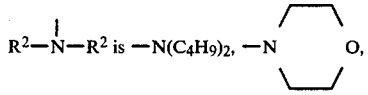

or $—N(iso—C_3H_7)_2$, and n is 2.

4. A composition according to claim 2 wherein said fluoroaliphatic radical-containing poly(oxyalkylene) has the general formula

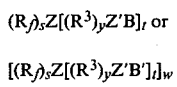

where
- $R_f$ is said fluoroaliphatic radical,
- Z is a linkage selected from aliphatic, aromatic, oxy, thio, carbonyl, sulfone, sulfoxy, phosphoxy, and amine groups and combinations thereof through which $R_f$ and $(R^3)_y$ are covalently bonded together,
- $(R^3)_y$ is a poly(oxyalkylene) moiety, $R^3$ being oxyalkylene with 2 to 4 carbon atoms, and y is an integer or number of at least 5 and can be as high as 100 or higher,
- B is a hydrogen atom or a monovalent terminal organic radical selected from acyl, alkyl, and aryl radicals,
- B' is B or a valence bond, with the proviso that at least one B' is a valence bond interconnecting a Z-bonded $(R^3)_y$ radical to another Z,
- Z' is a linkage selected from aliphatic, aromatic, oxy, thio, carbonyl, sulfone, sulfoxy, phosphoxy, and amine groups and combinations thereof through which B or B' and $(R^3)_y$ are covalently bonded together,
- s is an integer or number of at least 1 and can be as high as 25 or higher,
- t is an integer or number of at least 1 and can be as high as 60 or higher, and
- w is an integer or number greater than 1 and can be as high as 30 or higher.

5. A composition according to claim 2 wherein said fluorochemical poly(oxyalkylene) is the copolymer of $C_8F_{17}SO_2N(C_4H_9)C_2H_4O_2CCH=CH_2$ and $CH_2=CHCO_2(C_2H_4O)_{10}(C_3H_6O)_{22}(C_2H_4)_9C_2H_4O_2CCH=CH_2$.

6. A composition according to claim 2 wherein said fluorochemical guanidine is represented by the formula

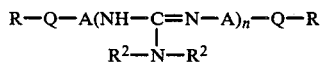

where R—Q is $C_8F_{17}SO_2N(C_2H_5)C_2H_4OCONH—$, A is $—C_6H_4CH_2C_6H_4—$,

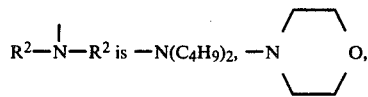

or $—N(iso—C_3H_7)_2$, and n is 2, and wherein said fluorochemical poly(oxyalkylene) is the copolymer of $C_8F_{17}SO_2N(C_4H_9)C_2H_4O_2CCH=CH_2$ and $CH_2=CHCO_2(C_2H_4O)_{10}(C_3H_6O)_{22}(C_2H_4O)_9C_2H_4O_2CCH=CH_2$.

7. A fiber finish comprising an organic solution or aqueous dispersion comprising the composition of claim 2.

8. The fiber finish according to claim 7 further comprising a fiber lubricant.

9. A method for imparting oil and water repellency to a fibrous substrate, which comprises treating the surface thereof with the fiber finish of claim 7.

10. In the manufacture of spun synthetic organic fibers wherein a fiber finish is applied to said fibers, the improvement comprising employing as said fiber finish the fiber finish of claim 8.

11. A fibrous substrate coated with the fluorochemical blend composition of claim 2.

12. A fibrous substrate according to claim 11 wherein said substrate is nylon carpet fiber.

13. A composition comprising a blend of:
(a) a normally solid, water-insoluble, fluorochemical guanidine composition which is a fluoroaliphatic radical-containing, substituted guanidine compound or composition comprising a mixture of said compounds, said compounds being represented by the general formula

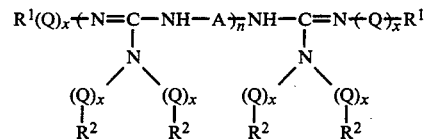

where n is 0 to 20, x is 0 to 1, $R^1$ and $R^2$ are hydrogen atoms, a monovalent fluoroaliphatic radical, $R_f$, having at least three fully fluorinated carbon atoms, or an organic radical selected from alkyl, cycloalkyl, and aryl groups and combinations thereof which can contain hetero moieties, the two $R^2$ groups of a guanidino moiety can be bonded together to form a cyclic structure with the adjacent N-atom of said guanidino moiety, A is a divalent organic linking group selected from alkylene, aralkylene, arylene, and polyoxyalkylene groups and combinations thereof, which can contain hetero moieties and said fluoroaliphatic radical, $R_f$, and Q is a divalent linking group selected from aliphatic, aromatic, oxy, thio, carbonyl, sulfone, sulfoxy, —N(CH$_3$)—, sulfonamido, carbonamido, sulfonamidoalkylene, carbonamidoalkylene, carbonyloxy, urethane, and urea groups, and combinations thereof, with the proviso that at least one fluoroaliphatic radical, $R_f$, is present in one or more of the $R^1$, $R^2$, and A groups, that where $R^1$ or $R^2$ is $R_f$, x is 1, and that when only one guanidino moiety is present and only two organic substituents are in said guanidino moiety, said substituents must be on different nitrogen atoms of the moiety, and when more than one guanidino moiety is present, said moieties are bonded together by divalent linking groups selected from the group consisting of alkylene, aralkylene, arylene, polyoxyalkylene, and combinations thereof and can contain said fluoroaliphatic radical; and (b) a normally liquid or low melting solid, water soluble or dispersible, fluoroaliphatic radical-containing poly(oxyalkylene), or composition comprising a mixture of such poly(oxyalkylenes), said poly(oxyalkylene) having one or more of said fluoroaliphatic radicals and one or more poly(oxyalkylene) moieties, said radicals and poly(oxyalkylene) moieties bonded together by linking groups selected from aliphatic, aromatic, oxy, thio, crbonyl, sulfone, sulfoxy, phosphoxy, and amine groups and combinations thereof.

14. A composition according to claim 2 wherein said fluorochemical guanidine is presented by the formula $$R-Q-A(NH-\underset{\underset{R^2-N-R^2}{|}}{C}-A)_n-Q-R$$

where R—Q is $C_8F_{17}SO_2N(C_2H_5)C_2H_4OCONH-$, A is $-CH_2C_6H_4CH_2-$, $R^2-\overset{|}{N}-R^2$ is $-N(C_4H_9)_2$, $-N\underset{\underset{}{\diagdown\_\diagup}}{\diagup^{\diagup\overline{\phantom{xx}}\diagdown}}O$, or $-N(iso-C_3H_7)_2$, and n is 1-6.

15. A composition according to claim 2 wherein said fluorochemical guanidine is represented by the formula $$R-Q-A(NH-\underset{\underset{R^2-N-R^2}{|}}{C=N}-A)_n-Q-R$$

where R—Q is $C_8F_{17}SO_2N(C_2H_5)C_2H_4OCONH-$, A is $-CH_2C_6H_4CH_2-$, $R^2-\overset{|}{N}-R^2$ is $-N(C_4H_9)_2$, $-N\underset{\underset{}{\diagdown\_\diagup}}{\diagup^{\diagup\overline{\phantom{xx}}\diagdown}}O$, or $-N(iso-C_3H_7)_2$, and n is 1-6, and wherein said fluorochemical poly(oxyalkylene) is the copolymer of $C_8F_{17}SO_2N(C_4H_9)C_2H_4O_2CCH=CH_2$ and $CH_2=CHCO_2(C_2H_4O)_{10}(C_3H_6O)_{22}(C_2H_4O)_9C_2H_4O_2CCH=CH_2$.

16. A composition according to claim 2 wherein said fluorochemical guanidine is represented by the formula $$R-Q-A(NH-\underset{\underset{R^2-N-R^2}{|}}{C=N}-A)_n-Q-R$$

where R—Q is $C_8F_{17}SO_2N(C_2H_5)C_2H_4OCONH-$, A is $-CH_2C_6H_4CH_2-$, $R^2-\overset{|}{N}-R^2$ is $-N(C_4H_9)_2$, and n is 1 to 6, and wherein said fluorochemical poly(oxyalkylene) is a copolymer of $C_8F_{17}SO_2N(C_4H_9)C_2H_4O_2CCH=CH_2$ and $CH_2=CHCO_2(C_2H_4O)_{10}(C_3H_6O)_{22}(C_2H_4O)_9C_2H_4O_2CCH=CH_2$.

17. A composition according to claim 2 wherein said fluorochemical poly(oxyalkylene) is a copolymer of $C_8F_{17}SO_2N(C_4H_9)C_2H_4O_2CCH=CH_2$, $CH_2=CHCO_2(C_2H_4O)_{10}(C_3H_6O)_3(C_2H_4O)_9C_2H_4OH$, and $CH_2CHCO_2(C_2H_4O)_{10}(C_3H_6O)_{22}(C_2H_4O)_9C_2H_4O_2CCH=CH_2$.

18. A composition according to claim 2 wherein said fluorochemical guanidine is represented by the formula $$R-Q-A(NH-\underset{\underset{R^2-N-R^2}{|}}{C=N}-A)_n-Q-R$$

where R—Q is $C_8F_{17}SO_2N(C_2H_5)C_2H_4OCONH-$, A is $-C_6H_4CH_2C_6H_4-$, $R^2-\overset{|}{N}-R^2$ is $-N(C_4H_9)_2$, $-N\underset{\underset{}{\diagdown\_\diagup}}{\diagup^{\diagup\overline{\phantom{xx}}\diagdown}}O$, or $-N(iso-C_3H_7)_2$, and n is 2, and wherein said fluorochemical poly(oxyalkylene) is the copolymer of $C_8F_{17}SO_2N(C_4H_9)C_2H_4O_2CCH=CH_2$, $CH_2=CHCO_2(C_2H_4O)_{10}(C_3H_6O)_{22}(C_2H_4O)_9C_2H_4OH$, and $CH_2=CHCO_2(C_2H_4O)_{10}(C_3H_6O)_{22}(C_2H_4O)_9C_2H_4O_2CCH=CH_2$.

19. A composition according to claim 2 wherein said fluorochemical guanidine is represented by the formula $$R-Q-A(NH-\underset{\underset{R^2-N-R^2}{|}}{C=N}-A)_n-Q-R$$

where R—Q is $C_8F_{17}SO_2N(C_2H_5)C_2H_4OCONH-$, A is $-CH_2C_6H_4CH_2-$, $R^2-\overset{|}{N}-R^2$ is $-N(C_4H_9)_2$, $-N\underset{\underset{}{\diagdown\_\diagup}}{\diagup^{\diagup\overline{\phantom{xx}}\diagdown}}O$, or $-N(iso-C_3H_7)_2$, and n is 1-6, and wherein said fluorochemical poly(oxyalkylene) is a copolymer of $C_8F_{17}SO_2N(C_4H_9)C_2H_4O_2CCH=CH_2$, $CH_2=CHCO_2(C_2H_4O)_{10}(C_3H_6O)_{22}(C_2H_4O)_9C_2H_4OH$, and $CH_2=CHCO_2(C_2H_4O)_{10}(C_3H_6O)_{22}(C_2H_4O)_9C_2H_4O_2CCH=CH_2$.

20. A composition comprising a blend of a fluorochemical guanidine represented by the formula $$R-Q-A(NH-\underset{\underset{R^2-N-R^2}{|}}{C=N}-A)_n-Q-R$$

wherein R—Q is $C_8F_{17}SO_2N(C_2H_5)C_2H_4OCONH-$, A is $-CH_2C_6H_4CH_2-$, $R^2-\overset{|}{N}-R^2$ is $-N(C_4H_9)_2$, and n is 1 to 6, and a fluorochemical poly(oxyalkylene) which is the copolymer of $C_8F_{17}SO_2N(C_4H_9)C_2H_4O_2CCH=CH_2$, $CH_2=CHCO_2(C_2H_4O)_{10}(C_3H_6O)_{22}(C_2H_4O)_9C_2H_4OH$, and $CH_2=CHCO_2(C_2H_4O)_{10}(C_3H_6O)_{22}(C_2H_4O)_9C_2H_4O_2CCH=CH_2$.

* * * * *

UNITED STATES PATENT AND TRADEMARK OFFICE
CERTIFICATE OF CORRECTION

PATENT NO. : 4,565,641
DATED : January 21, 1986
INVENTOR(S) : JOHN CHENG-CHUNG CHANG and KATHRYN L. WILLIAMS It is certified that error appears in the above-identified patent and that said Letters Patent is hereby corrected as shown below:

Col. 4, line 19, "$C_8F_{17}SO_2N[C_2H_4OCONHC_6H_3(CH_3)-_2$" should read --$C_8F_{17}SO_2N\{C_2H_4OCONHC_6H_3(CH_3)\}_2$--.

Col. 6, line 55, "supra" should read --<u>supra</u>--.

Col. 11, line 4, "commposition" should read --composition--.

Col. 15, line 43, "prcent" should read --percent--.

Col. 18, line 36, "TABLE 7" was omitted; it should precede --<u>Amount Fluorine on Carpet</u>--.

Col. 18, line 44, "73/30" should read --70/30--.

Signed and Sealed this

Eighth Day of July 1986

[SEAL]

Attest:

DONALD J. QUIGG

Attesting Officer

Commissioner of Patents and Trademarks